United States Patent
Handerek

(10) Patent No.: US 9,244,009 B2
(45) Date of Patent: *Jan. 26, 2016

(54) DISTRIBUTED OPTICAL FIBRE SENSOR

(71) Applicant: Fotech Solutions Limited, London (GB)

(72) Inventor: Vincent Handerek, Grays (GB)

(73) Assignee: FOTECH SOLUTIONS LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/797,367

(22) Filed: Jul. 13, 2015

(65) Prior Publication Data

US 2015/0323455 A1    Nov. 12, 2015

Related U.S. Application Data

(63) Continuation of application No. 13/992,578, filed as application No. PCT/GB2011/052409 on Dec. 6, 2011, now Pat. No. 9,110,018.

(30) Foreign Application Priority Data

Dec. 8, 2010    (GB) .................................. 1020827.0

(51) Int. Cl.
*G01N 21/47*    (2006.01)

(52) U.S. Cl.
CPC .... *G01N 21/474* (2013.01); *G01N 2201/06113* (2013.01); *G01N 2201/088* (2013.01)

(58) Field of Classification Search
CPC . G01N 21/474; G01N 21/4738; G01N 21/55; G01N 21/57
USPC .......................................................... 356/446
See application file for complete search history.

(56) References Cited

U.S. PATENT DOCUMENTS

| 5,096,277 | A | 3/1992 | Kleinerman |
| 5,194,847 | A | 3/1993 | Taylor et al. |
| 5,965,877 | A | 10/1999 | Wood et al. |
| 6,380,534 | B1* | 4/2002 | Farhadiroushan . G01D 5/35364 250/227.14 |
| 7,350,972 | B2* | 4/2008 | Seebacher .............. G01K 11/32 356/337 |

(Continued)

FOREIGN PATENT DOCUMENTS

| EP | 0213872 A2 | 3/1987 |
| EP | 0872721 A1 | 10/1998 |

(Continued)

OTHER PUBLICATIONS

Dakin et al., "Review Article; Multiplexed and distributed optical fibre sensor systems," J. Phys. E:Sci Instrum; vol. 20; pp. 954-967; Mar. 4, 1987.

(Continued)

*Primary Examiner* — Tarifur Chowdhury
*Assistant Examiner* — Md Rahman
(74) *Attorney, Agent, or Firm* — K&L Gates LLP

(57) ABSTRACT

There is disclosed a distributed optical fiber sensor arranged to deliver probe light pulses of different wavelengths into corresponding different sensing optical fibers, and to determine one or more parameters as functions of position along each of the sensing fibers from detected backscattered light of each corresponding wavelength. In another arrangement, the different wavelengths are directed in different corresponding directions around a loop of sensing optical fiber.

20 Claims, 4 Drawing Sheets

(56) References Cited

U.S. PATENT DOCUMENTS

| | | |
|---|---|---|
| 2004/0011950 A1 | 1/2004 | Harkins |
| 2004/0196664 A1 | 10/2004 | Renard et al. |
| 2010/0014071 A1 | 1/2010 | Hartog |
| 2011/0151550 A1* | 6/2011 | Sagner .................. C12Q 1/6851 435/287.2 |

FOREIGN PATENT DOCUMENTS

| | | | |
|---|---|---|---|
| FR | 2520114 | A1 | 7/1983 |
| GB | 1419701 | | 12/1975 |
| GB | 2374928 | | 5/2008 |
| GB | 2443661 | | 9/2010 |
| GB | 2469012 | | 9/2010 |
| JP | 02151742 | | 6/1990 |
| JP | 2000082187 | A | 3/2000 |
| JP | 2004347554 | | 12/2004 |
| WO | 9830881 | A1 | 7/1998 |
| WO | 9912287 | A1 | 3/1999 |
| WO | 2006045340 | A1 | 5/2006 |
| WO | 2007141464 | A1 | 12/2007 |
| WO | 2008056143 | A1 | 5/2008 |
| WO | 2008081157 | A1 | 7/2008 |
| WO | 2010036360 | A1 | 4/2010 |

OTHER PUBLICATIONS

Horiguchi, et al., "Development of a Distributed Sensing Technique Using Brillouin Scattering," Journal of Lightwave Technology; vol. 13; No. 7; pp. 1296-1302; Jul. 1995.

Senior et al., "Wavelength Division Multiplexing in Optical Fibre Sensor Systems and Networks: A Review," Optics & Laser Technology; vol. 22; No. 2; pp. 113-126; Apr. 1990.

Search Report for British Application No. GB1020827.0; Mar. 8, 2011 Search Date; 2 pages.

Search Report for British Application No. GB1020827.0; Aug. 23, 2011 Search Date; 2 pages.

International Search Report for PCT/GB2011/052409; Search completed Jul. 12, 2012; Search mailed Jul. 23, 2012; 6 pages.

Written Opinion of the International Searching Authority for PCT/GB2011/052409; Mailed Jul. 23, 2012; 9 pages.

* cited by examiner

DISTRIBUTED OPTICAL FIBRE SENSOR

CROSS REFERENCE TO RELATED APPLICATIONS

This is a continuation of U.S. application Ser. No. 13/992,578, filed on Jun. 7, 2013, which is the national phase under 35 U.S.C. §371 of International Application No. PCT/GB2011/052409, filed on Dec. 6, 2011, which claims priority to and the benefit of GB 1020827.0, filed on Dec. 8, 2010, the entire contents of each of which are incorporated by reference herein.

The present invention relates to distributed optical fibre sensors, in which one or more physical parameters are sensed as a function of position along a sensing optical fibre from the properties of probe light backscattered within the sensing fibre. In particular, but not exclusively, the invention relates to optical time domain reflectometry (OTDR) sensors for use in sensing vibration, and such sensors which use phase sensitive OTDR techniques such as through the detection of coherent Rayleigh noise, or other interferometric techniques.

INTRODUCTION

Distributed optical fibre sensing is a well known approach to providing information about environmental conditions surrounding a sensing optical fibre. Fully-distributed sensing in principle provides spatially resolved information from every point along the fibre. Variables that can be sensed include temperature, static strain, pressure, and vibration.

One such technique detects variations in refractive index, induced by a physical forcing such as vibration, in the coherent Rayleigh noise profile of light backscattered within a sensing optical fibre interrogated by an optical source of limited bandwidth. Such Rayleigh noise profiles arise from interference between the many components of the backscattered light originating from different points along a portion of the sensing optical fibre illuminated by the optical source. Such techniques are described, for example, in WO2008/056143.

Another such technique detects variations in fibre temperature and strain through their effects on Brillouin scattering of probe light launched into the fibre. Such techniques are described, for example, in Horiguchi et al., Journal of Lightwave Technology, vol. 13, no. 7, July 1995.

It would be desirable to address problems and limitations of the related prior art.

SUMMARY OF THE INVENTION

Accordingly, the invention provides a distributed optical fibre sensor for determining one or more parameters as functions of position along a plurality of sensing optical fibres from properties of probe light backscattered within the sensing optical fibres, for example to monitor the environment along each sensing optical fibre, the sensor comprising:

a probe light source arranged to generate probe light pulses each at one of a plurality of optical wavelengths; a coupler arranged to receive the probe light pulses from the probe light source and to route pulses of each wavelength into a different corresponding one of said sensing optical fibres, and to collect probe light backscattered within the sensing fibres; a detector arranged to receive the collected backscattered light and to separately detect light of each of said different wavelengths in said collected backscattered light; and an analyser arranged to determine said one or more parameters as functions of position along each of the sensing fibres from said detected backscattered light of each corresponding wavelength.

Such a sensor can make use of optical pathways and components common to all of the wavelengths to reduce the size, complexity and cost of implementing interrogation of multiple sensing fibres.

The invention can also be applied to a single loop of sensing fibre, with two interrogated pathways being opposite directions around the same loop. Accordingly, the invention also provides a distributed optical fibre sensor for determining one or more parameters as functions of position in both directions along a loop of sensing optical fibre from properties of probe light backscattered within the sensing optical fibre, the sensor comprising: a probe light source arranged to generate probe light pulses each at one of two optical wavelengths; a coupler arranged to receive the probe light pulses from the probe light source and to direct pulses of each wavelength into the sensing optical fibre in a different corresponding direction, and to collect probe light backscattered within the sensing optical fibre; a detector arranged to receive the collected backscattered light and to separately detect light of each of said different wavelengths in said collected backscattered light; and an analyser arranged to determine said one or more parameters as functions of position in each direction along the sensing optical fibre from said detected backscattered light of each corresponding wavelength. When applied to a loop in this way, a single break in the sensing fibre can be accommodated without loss of function by interrogating the fibre in each direction as far as the break.

The coupler may be a wavelength multiplexer/demultiplexer component arranged to receive the probe light pulses of all of the plurality of optical wavelengths, and to demultiplex each wavelength onto a different sensing fibre or different direction around the fibre loop. A single connector waveguide maybe used to deliver the pulses of all of the wavelengths to the coupler and to carry the collected backscattered light of all of the wavelengths from the coupler for delivery to the detector.

The probe light pulses may be conditioned using one or more source optical conditioning components through which the probe light pulses of all of the plurality of wavelengths are passed before being launched into the sensing optical fibre or fibres. Similarly, the backscattered light may be conditioned using one or more detector optical conditioning components through which all of the collected backscattered light is passed before being detected. Such optical conditioning components may include optical amplifiers, bandpass filters and similar.

The probe light pulses of the plurality of wavelengths may be generated using a switched wavelength laser, or using separate correspondingly tuned laser sources, or by applying wavelength shifting techniques to the light from a single, master laser source. In particular, the probe light source may be arranged to generate the probe light pulses such that backscattered light of at least two of the plurality of wavelengths is detected by the detector at the same time. Note that a single probe light pulse of a few nanoseconds duration launched into a sensing optical fibre will typically give rise to backscattered light spread over a few microseconds, depending on the length of the sensing optical fibre. In order to increase the proportion of time within which each sensing fibre is interrogated, the probe light source may therefore be arranged to generate the probe light pulses such that backscattered light of more than one, and optionally all of the plurality of wavelengths at least partially overlaps at the detector.

The parameter may be a parameter of the environment around the sensing fibre. The sensor may be used to detect a variety of parameters, for example vibration, temperature, pressure, and strain at the sensor fibre or fibres. The analyser may be arranged to determine the same parameter in respect of each of said sensing fibres or loop direction, or to determine different parameters on some or all of the fibres or loop directions. Such parameters may be detected using a variety of optical techniques which are known in the art. The invention may, for example be implemented such that the detector detects coherent Rayleigh noise, Rayleigh backscatter, Raman scattering or Brillouin scattering at one or more of said plurality of wavelengths, and the analyser determines one or more of said parameters from properties of the coherent Rayleigh noise, Rayleigh backscatter, Raman scattering or Brillouin scattering.

The invention may be used to monitor a variety of environments and structures, such as oil, gas and other geological wells, along a plurality of branches of such wells, pipelines, building structures, and along security perimeters.

The invention also provides methods corresponding to the apparatus discussed above, for example a method of operating a distributed optical fibre sensor to determine one or more parameters as functions of position along a plurality of sensing optical fibres from properties of probe light backscattered within the sensing optical fibres, to thereby monitor the environments of said sensing optical fibres, comprising: operating a probe light source to generate probe light pulses each at one of a plurality of optical wavelengths; coupling the probe light pulses of each wavelength into a different corresponding one of said sensing optical fibres; collecting probe light backscattered within the sensing optical fibres; separately and simultaneously detecting light of each of said different wavelengths in said collected backscattered light; and determining said one or more parameters as functions of positions along each of the sensing optical fibres from said detected backscattered light of each corresponding wavelength. The invention may similarly be applied as a method to a loop of sensing fibre with different probe light pulse wavelengths being used in each direction around the loop.

The probe light pulses may be delivered to the sensing optical fibre or fibres and the backscattered probe light may be collected and combined from the sensing optical fibre or fibres by a wavelength multiplexer/demultiplexer component. The timing of the generation of probe light pulses by the probe light source may be controlled such that at least some of the collected backscattered light contains light of more than one of said wavelengths.

The steps of operating the probe light source and detecting the backscattered light may be implemented such that coherent Rayleigh noise is detected in the backscattered light, and the step of determining comprises determination of said one or more parameters from properties of the coherent Rayleigh noise. The one or more determined parameters may include a parameter representative of vibration in the one or more corresponding sensing optical fibres.

In implementing any of the aspects mentioned above, the invention may also provide a method of determining parameters along a plurality of extended paths, comprising disposing a sensing optical fibre along each of said paths, coupling the sensing optical fibres to a single interrogator unit, using the interrogator unit to launch probe light pulses of a different wavelength along each of said sensing optical fibres, and using the interrogator unit to detect and analyse the probe light backscattered within the sensing optical fibres to determine said parameters. This method may also be applied to interrogating in opposite directions along a loop of sensing optical fibre.

BRIEF SUMMARY OF THE DRAWINGS

Embodiments of the invention will now be described, by way of example only, with reference to the accompanying drawings, of which.

DETAILED DESCRIPTION OF EMBODIMENTS

Figure 1:
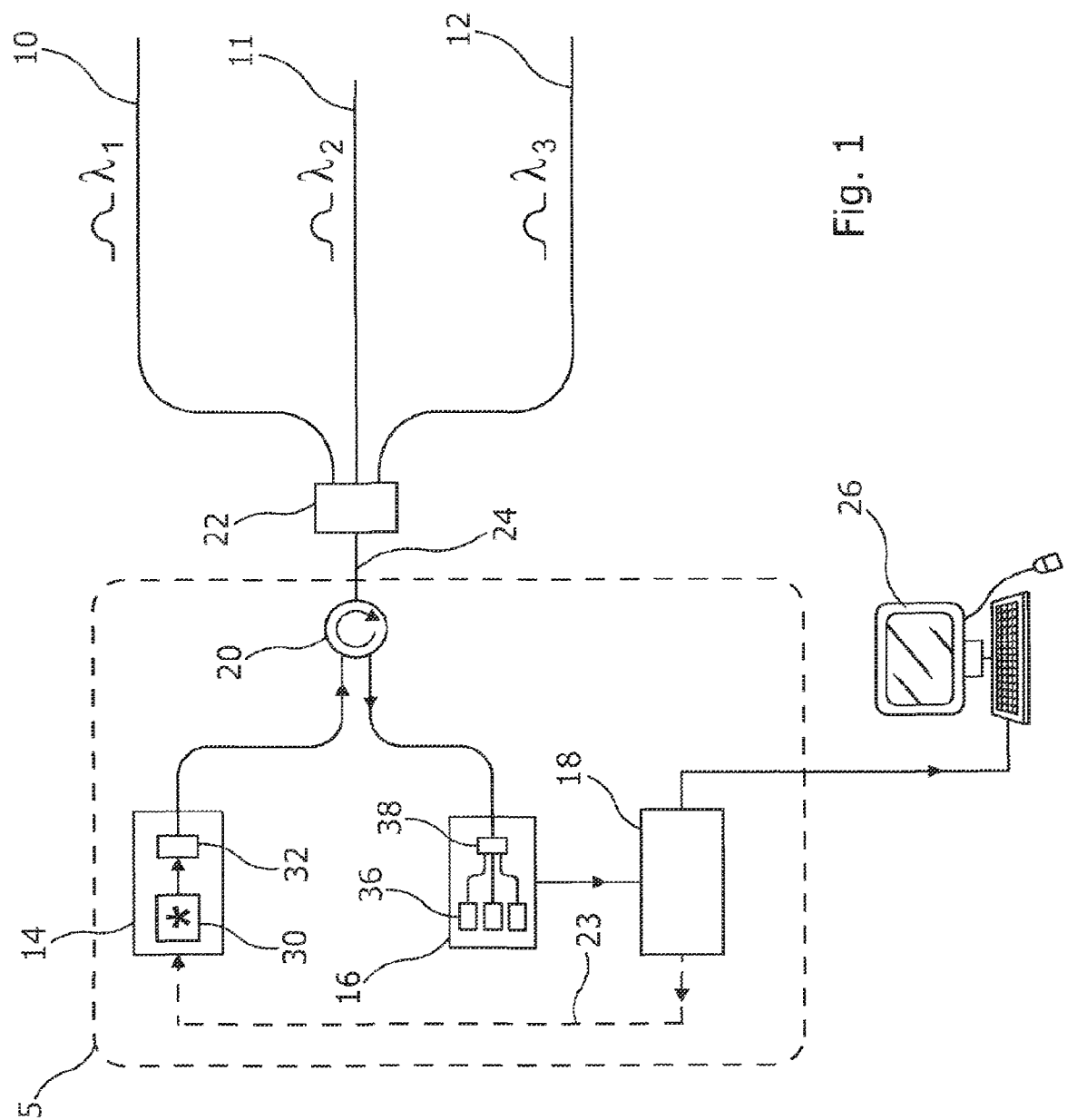
FIG. 1 illustrates a distributed optical fibre sensor embodying the invention.

Referring to FIG. 1 there is illustrated a distributed optical fibre sensor arranged to sense one or more physical parameters as a function of position along part or all of each a plurality of sensing optical fibres 10, 11, 12 using time domain reflectometry, or another reflectometry technique. An interrogator unit 5 of the sensor includes a probe light source 14 for generating probe light pulses of suitable timings, shapes and wavelengths, a detector 16 for detecting probe light resulting from the probe light pulses being backscattered within the sensing fibres 10, 11, 12, and an analyser 18 for processing data, such as properties of the backscattered and detected light, which has been received from the detector.

The probe light source forms probe light pulses, each pulse having an optical wavelength selected from a plurality of different wavelengths. Three such wavelengths are used in the figure, shown as $\lambda_1$, $\lambda_2$ and $\lambda_3$. The probe light pulses are forwarded to an optical circulator 20 and from there on to an optical coupler 22. The coupler provides a wavelength multiplex/demultiplex function, delivering probe light pulses of each of the wavelengths to a corresponding one of the sensing fibres 10, 11, 12 as shown in the figure. In FIG. 1 the circulator 20 is shown as forming part of the interrogator unit 5, and the coupler as being external to the interrogator unit. However, other arrangements may be used as appropriate to the implementation, for example by including the coupler within the interrogator unit 5.

Probe light backscattered within the sensing fibres 10, 11, 12, is combined together at the coupler 22, and delivered from there to the circulator 20 which passes the collected light on to the detector 16. Conveniently, the probe light pulses and collected backscattered light may be coupled between the circulator 20 and coupler 22 using a single connector waveguide 24, typically a single optical fibre, and each of the probe light source and the detector may similarly be linked to the circulator using single optical fibres.

The analyser 18 outputs analysis results such as a determination of the one or more physical parameters, and in FIG. 1 this output is passed to a computer display 26, although various other types of output mechanism may be used. The analyser 18 may also use data derived from the detected backscatter to provide control signals 23 to the probe light source 14. A variety of control signals may be provided, including signals controlling the durations, timings and wavelengths of probe light pulses, as required. In alternative embodiments, the control functions may be implemented separately to the analyser 18, for example in a separate controller element (not shown in the figure).

The probe light source is arranged to generate the probe light pulses of different wavelengths according to particular timing schemes. Because a different wavelength is used to interrogate each sensing optical fibre, it is not necessary to wait until all the backscattered light of one pulse has arrived at the detector before launching another probe light pulse. Pulses of different wavelengths may be generated at the same time so as to overlap, or so that backscattered light from one or more pulses of different wavelengths, or pulses of all of the wavelengths, overlap at the detector. In particular, the detector may be arranged to separately detect backscattered light of each of the wavelengths, and more particularly to separately and simultaneously detect backscattered light of more than one or of all of the wavelengths.

The probe light source contains one or more laser sources 30 to generate the probe light pulses. For example, the pulses of all of the different wavelengths may be generated using a single switched wavelength laser source, suitably controlled, or pulses of the different wavelengths may be generated using discrete separate laser sources, or using a single laser with a wavelength shifting method. The probe light pulses are conditioned in the probe light source by one or more source optical conditioning components 32. If multiple laser sources are used then some of these components may be specific to one or more of the lasers, but typically one or more of the source optical conditioning components will be used to condition pulses of all of the wavelengths.

The detector 16 preferably uses a different detector element 36 to detect backscattered light of each of the different probe light wavelengths. The detector elements may be, for example, suitable photodiodes, with wavelength selective components used to direct the collected light to the appropriate detector. The backscattered light is conditioned in the detector using one or more detector optical conditioning components, and typically at least one of the detector optical conditioning components is used to condition backscattered light of all of the generated wavelengths. Use of a common optical pathway and components common to all of the wavelengths simplifies the interrogator and reduces costs.

The optical conditioning components in the interrogator, including individual components which are used to condition light of all of the wavelengths, may include optical amplifiers, band pass filters, and other components.

The sensing fibres may all be of the same type, or may be of different types including, without limitation, single mode fibre, multimode fibre, fibre with high birefringence, and fibre especially adapted or encased so as to respond or enhance the response to changes in one or more of pressure, temperature, and other parameters which are to be measured.

A variety of interrogation techniques may be used, for example depending on the parameters which are to be measured, and the probe light source 14, detector 16, sensing fibres and other components of the sensor may be adapted accordingly. For example, the sensing fibres may be interrogated using techniques based on Rayleigh backscatter, coherent Rayleigh noise, Raman scattering, and Brillouin scattering. In some embodiments all of the sensing fibres are interrogated using the same technique, or the same combination of techniques, and in other embodiments different techniques or combinations of techniques are used on some or all of the sensing fibres. The sensor may use selected ones of these techniques as appropriate to measure parameters such as vibration, static or transient strain, temperature, and pressure.

Figure 2A:
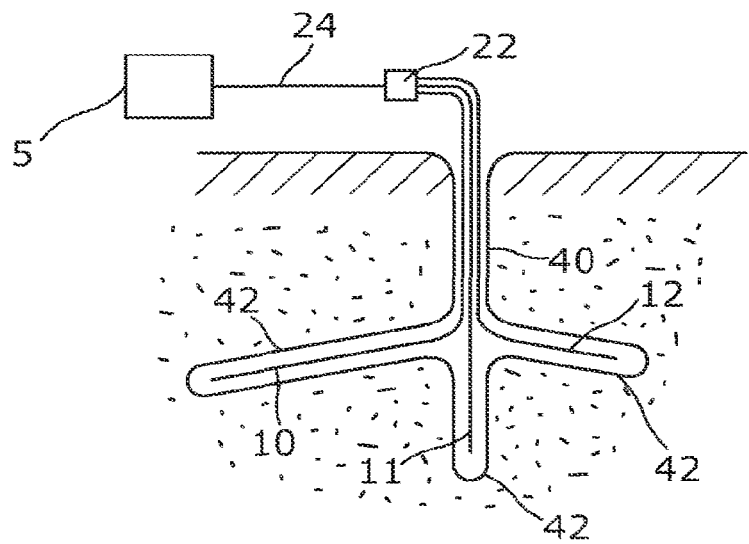
FIGS. 2a, 2b and 2c show some geological well applications for use of the invention.
Figure 2B:
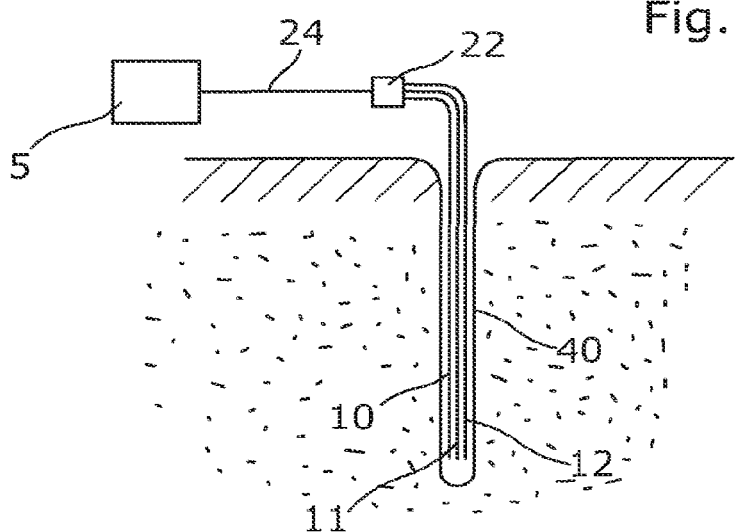
Figure 2C:
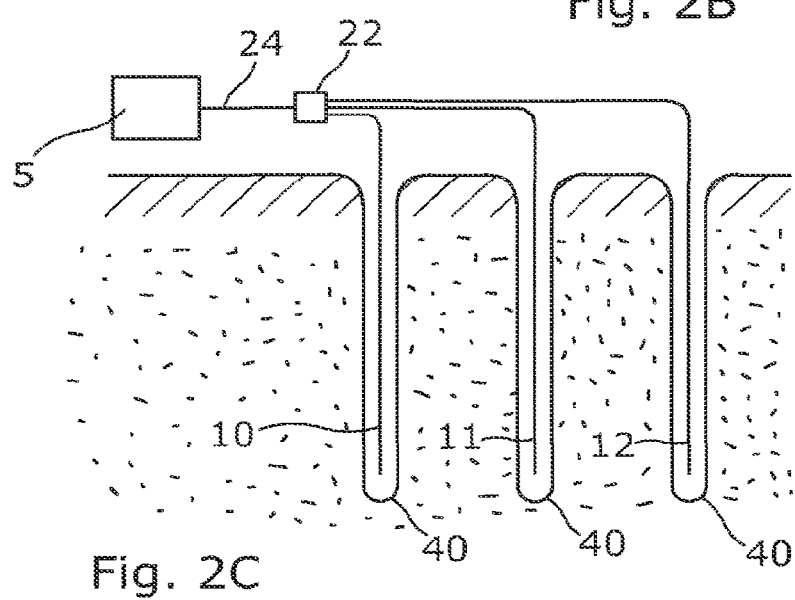

The arrangement of FIG. 1 can be used in a variety of situations. FIG. 2a illustrates the sensor being used to monitor multiple branches of a single geological borehole 40, such as an oil or gas well. Each branch 42 is monitored using a different one of the sensing fibres. In FIG. 2b multiple sensing fibres are used to monitor the same borehole 40, for example to provide redundancy, or to use different sensing fibres to sense different parameters. In FIG. 2c multiple sensing fibres are used to monitor separate boreholes 40.

Figure 3:
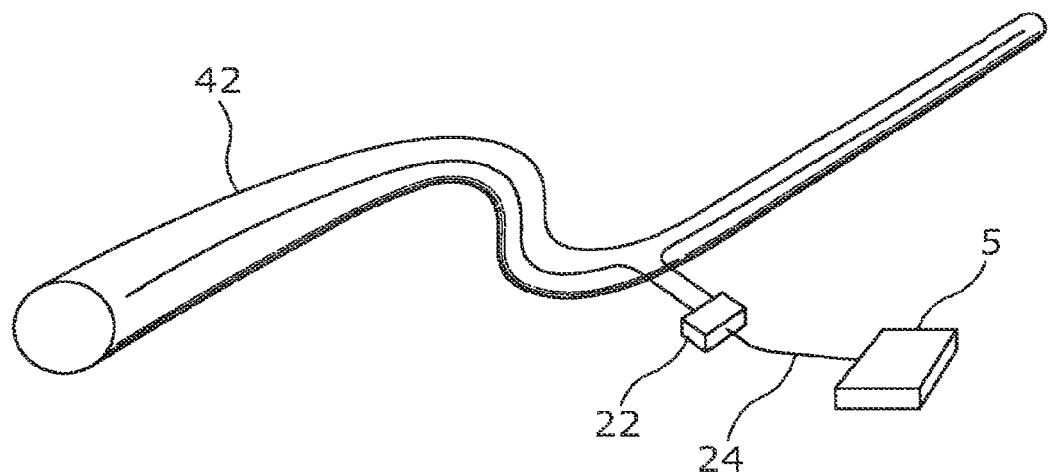
FIG. 3 shows an embodiment of the invention using a different sensing optical fibre disposed in each direction along an elongate structure such as a pipeline.

In other applications, the multiple sensing fibres are used to monitor along different pathways across or through a building structure or infrastructure component, such as a bridge, a pipe line or a roadway. FIG. 3a illustrates use of the invention to increase the length of a pipeline 42 which can be monitored using a single interrogator unit 5, by directing sensing optical fibres in opposite directions along the pipeline from the interrogator unit. A similar arrangement can be used for other extended structures, or for security/intrusion monitoring across long stretches of land or fences and other types of borders.

Figure 4:
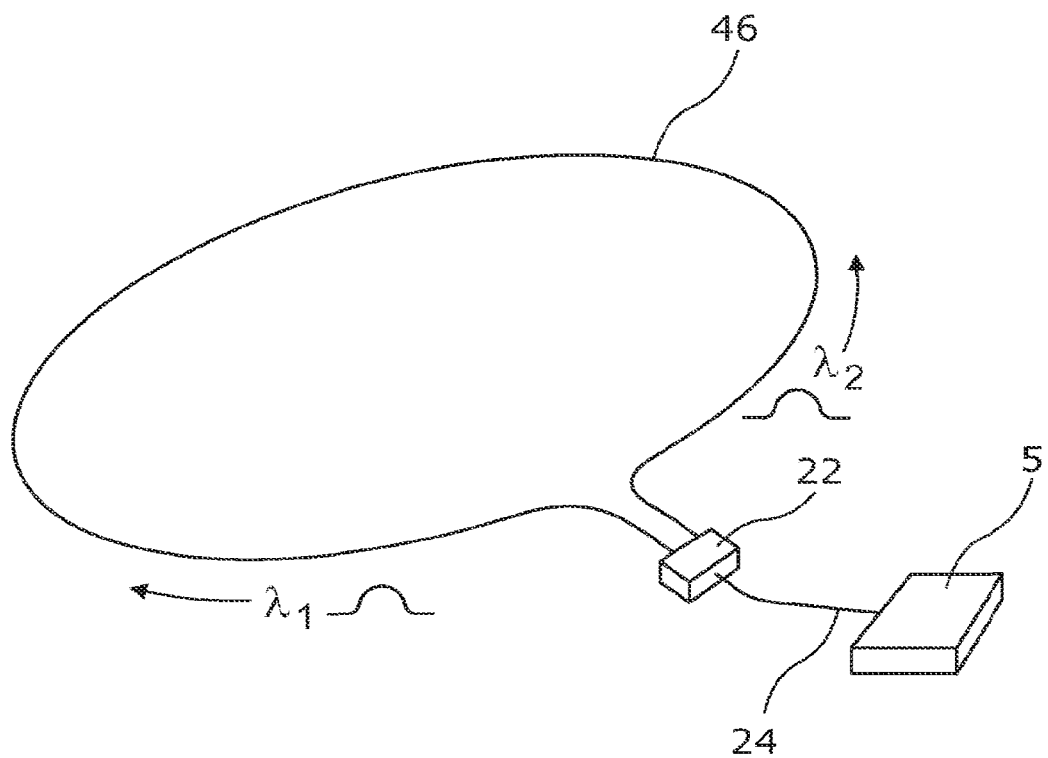
FIG. 4 shows the invention applied to a loop of sensing optical fibre.

In FIG. 4, an open loop 46 of sensing optical fibre is disposed through an environment to be sensed, for example along a borehole, fence, along the ground etc. Probe light pulses of one optical wavelength are launched into the loop 46 in one direction, and pulses of a second wavelength are launched into the loop 48 in the opposite direction. From the point of view of the coupler 22 and interrogator 5 the loop appears to be two separate fibres extending individually through the environment. However, the loop topology allows interrogation along the full length of the sensing fibre to continue even when the loop is broken in one place.

Figure 5:
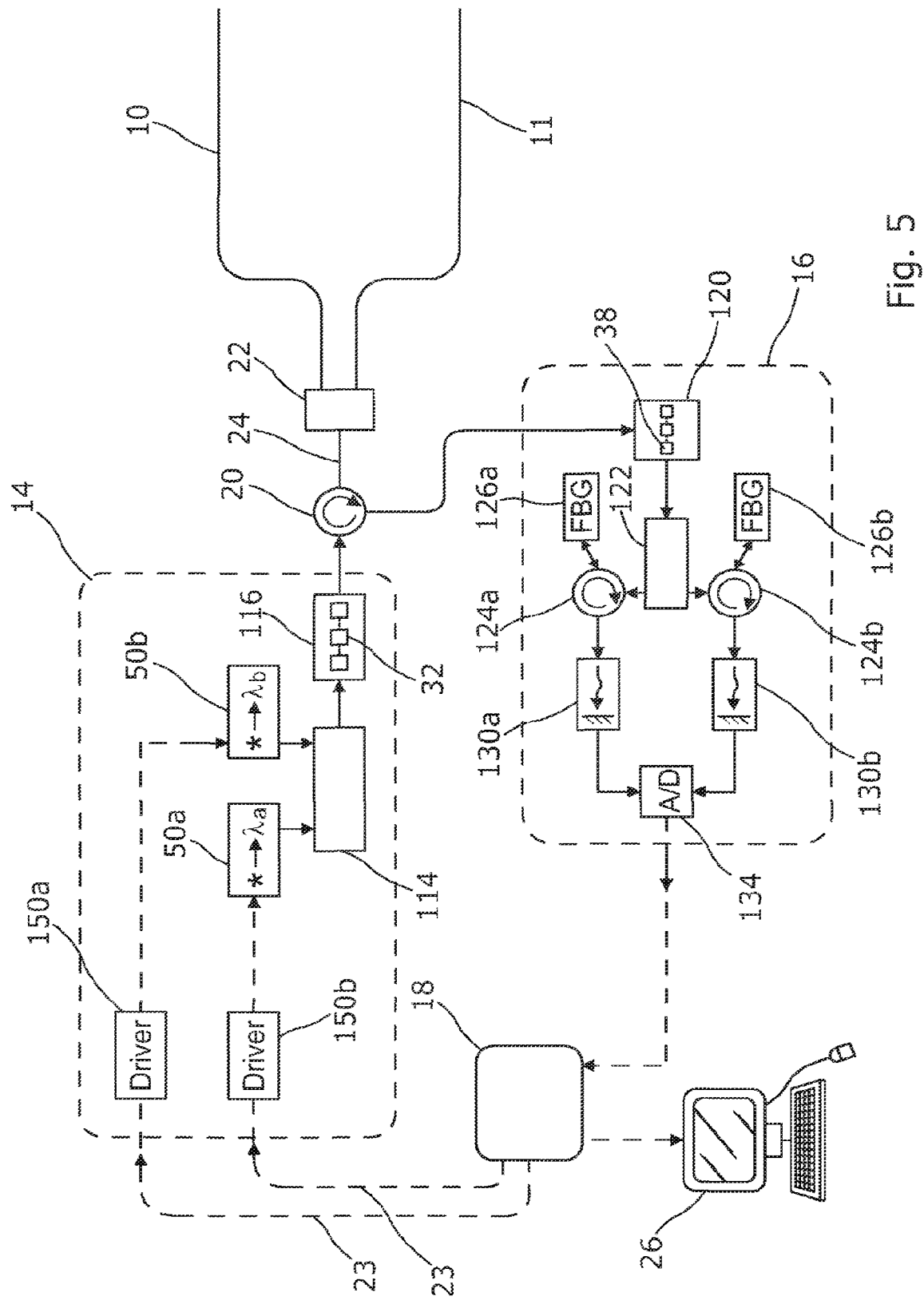
FIG. 5 shows how the sensor of FIGS. 1 to 4 can be implemented in more detail.

FIG. 5 shows details of optics and electronics which may be used for putting into effect the distributed optical fibre sensor described above.

Two separate optical sources 50a and 50b are shown within the probe light source 14, each optical source emitting a narrow band of wavelengths centred at $\lambda_a$ and $\lambda_b$ respectively. It would alternatively be possible to use a single, wavelength switched source, or a combination of sources with switchable and fixed wavelengths. Since two separate optical sources are shown in this embodiment, a wavelength combiner component 114 is required to route the two signal wavelengths onto a common optical path. If a wavelength switched source were to be used alone, then this component would not be required. For convenience of implementation, the wavelengths $\lambda_a$ and $\lambda_b$ used in the system could lie within the operating band of typical erbium-doped fibre amplifiers, between 1528 nm to 1562 nm, and the optical sources could be distributed-feedback laser diodes.

Once combined, the two signal wavelengths are then fed through an optical conditioning chain 116 whose function is to amplify the light to suitable power levels and to provide optical filtering to avoid the deleterious effects of amplified spontaneous emission (ASE) from the amplifier elements. This optical conditioning chain comprises optical components 32 through which probe light pulses of both pulse wavelengths pass. Typically, peak powers of the order of 1 W might be delivered to the sensing fibres 10, 11 and the ASE suppression bandwidth might be ~0.2 nm. Light emerging from the optical conditioning chain 116 is directed to the optical circulator 20 that serves to route probe light from the probe light source 14 to the coupler 22 which is provided by a wavelength multiplexer/demultiplexer component. The coupler 22 couples the probe light pulses of each wavelength into a different one of the sensing fibres 10, 11 and light from the sensing fibres back to the circulator 20 which couples the light from the sensing fibres to the detector 16.

Backscattered light returning from the sensing fibres through the coupler and circulator is directed into the detector 16, and in particular into an optical signal conditioning chain 120. This chain contains further amplification and filtering components 38 required to increase the received signal powers to levels suitable for low-noise detection. Following passage through the signal conditioning chain 120, the two signal wavelengths $\lambda_a$ and $\lambda_b$ are separated by the wavelength demultiplexing component 122. After separation, the two signal wavelengths $\lambda_a$ and $\lambda_b$ are each further filtered to a narrow band using components 124a, 124b and 126a, 126b respectively. In this embodiment, the narrow band filters are fibre Bragg gratings with approximately 80 pm reflection bandwidth. Finally, each wavelength is received by its own photodetector, 130a and 130b respectively. Conveniently, PIN photodiodes may be used for this purpose.

The signals from each photodetector 130a, 130b are digitized by the data acquisition unit 134 and fed to the analyser 18, which controls the optical sources 110a and 110b via driver circuits 150a and 150b. Apart from providing accurately timed electrical pulses to the optical sources to control probe light pulse timing and length, these driver circuits may also serve to fine-tune the wavelength of the optical sources. This can be achieved, for example, by control of laser temperature. In possible alternative embodiments, fine-tuning of the centre wavelength of different probe light pulses might be accomplished by controlled filtering either before the unconditioned probe light enters the wavelength combiner 114 or after leaving the wavelength demultiplexer 122. In the latter case, the centre wavelength of one or both of the fibre Bragg gratings could be thermally tuned. In another possible embodiment, fine control of wavelength might alternatively be achieved by phase or frequency modulation of light using a radio frequency optical modulator together with appropriate filtering.

Based on analysis of the backscattered probe light, the analyser 18 provides control signals to the driver circuits 150a, 150b, for example to control probe light pulse length and probe pulse wavelength as required.

Although various embodiments of the present invention have been described above, it should be understood that they have been presented by way of example only, and not limitation. For example, the skilled person will appreciate that the optical, electronic and data processing functionality of the distributed optical fibre sensor can be implemented and distributed across different functional or physical units in various ways according to convenience and implementation objectives.

It will be understood by those skilled in the relevant art(s) that various changes in form and details may be made therein without departing from the spirit and scope of the invention as defined in the appended claims.

The invention claimed is:

1. A distributed optical fibre sensor for determining one or more parameters as functions of position along a plurality of sensing optical fibres from properties of probe light backscattered within the sensing optical fibres, the sensor comprising:
   - a probe light source arranged to generate probe light pulses each at one of a plurality of optical wavelengths;
   - a wavelength multiplexer/demultiplexer component arranged to receive the probe light pulses from the probe light source and to direct pulses of each wavelength into a different corresponding one of said sensing optical fibres, and to collect probe light backscattered within the sensing optical fibres;
   - a detector arranged to receive the collected backscattered light and to separately detect light of each of said different wavelengths in said collected backscattered light; and
   - an analyser arranged to determine said one or more parameters as functions of position along each of the sensing optical fibres from said detected backscattered light of each corresponding wavelength.

2. The sensor of claim 1 wherein the wavelength multiplexer/demultiplexer component is arranged to receive the probe light pulses of all of the plurality of optical wavelengths along a connector waveguide and to output all of the plurality of optical wavelengths of the collected backscattered light along the connector waveguide.

3. The sensor of claim 1 wherein the probe light source is arranged to generate said probe light pulses such that backscattered light of at least two of the plurality of wavelengths is detected by the detector at the same time.

4. The sensor of claim 1 wherein the probe light source is arranged to generate said probe light pulses such that backscattered light of all of the plurality of wavelengths is detected by the detector at the same time.

5. The sensor of claim 1 arranged such that the detector detects at least one of Rayleigh, Raman and Brillouin backscatter at each of said plurality of wavelengths, and the analyser determines said one or more parameters from said at least one of Rayleigh, Raman and Brillouin backscatter.

6. The sensor of claim 1 arranged such that the detector detects coherent Rayleigh noise at one or more of said plurality of wavelengths, and the analyser determines one or more of said parameters from properties of the coherent Rayleigh noise.

7. The sensor of claim 1 wherein each of the one or more parameters represents one of: vibration; temperature; pressure; and strain.

8. The sensor of claim 1 wherein the analyser is arranged to determine the same parameter in respect of each of said sensing fibres.

9. The sensor of claim 1 wherein the probe light pulses are conditioned using one or more source optical conditioning components through which the probe light pulses of all of the plurality of wavelengths are passed before being launched into the sensing optical fibre or fibres.

10. The sensor of claim 9 wherein one or more of the optical conditioning components include at least one of: an optical amplifier; and a bandpass filter.

11. The sensor of claim 1 wherein the backscattered light is conditioned using one or more detector optical conditioning components through which all of the collected backscattered light is passed before being detected.

12. The sensor of claim 1 further comprising said plurality of sensing fibres, the sensing fibre(s) being disposed in or along at least one of: a well; a plurality of branches of a well; a pipeline; a building structure; a security perimeter; and in opposite directions along an elongate pathway.

13. The sensor of claim 1 wherein probe light pulses of the plurality of wavelengths are generated using a switched wavelength laser.

14. The sensor of claim 1 wherein the probe light pulses of each of the plurality of wavelengths are generated using a separate correspondingly tuned laser.

15. A method of operating a distributed optical fibre sensor to determine one or more parameters as functions of position along a plurality of sensing optical fibres from properties of probe light backscattered within the sensing optical fibres, comprising:

operating a probe light source to generate probe light pulses each at one of a plurality of optical wavelengths;

coupling the probe light pulses of each wavelength into a different corresponding one of said sensing optical fibres;

collecting probe light backscattered within the sensing optical fibres;

separately detecting light of each of said different wavelengths in said collected backscattered light; and determining said one or more parameters as functions of position along each of the sensing optical fibres from said detected backscattered light of each corresponding wavelength, wherein the probe light pulses are delivered to the sensing optical fibres and the backscattered probe light is collected and combined from the sensing optical fibres by a wavelength multiplexer/demultiplexer component.

16. The method of claim 15 comprising controlling the timing of the generation of probe light pulses by the probe light source such that at least some of the collected backscattered light contains light of more than one of said wavelengths.

17. The method of claim 15 comprising separately and simultaneously detecting backscattered light of all of said different wavelengths.

18. The method of claim 15 comprising determining said one or more parameters from properties of at least one of Rayleigh, Brillouin and Raman backscatter of said probe light pulses.

19. The method of claim 15 wherein the steps of operating the probe light source and detecting the backscattered light are arranged such that coherent Rayleigh noise is detected in the backscattered light, and the step of determining comprises determining said one or more parameters from properties of the coherent Rayleigh noise.

20. The method of claim 15 wherein the one or more parameters include a parameter representative of vibration in the one or more corresponding sensing optical fibres.

* * * * *